US006221986B1

(12) United States Patent
Commereuc et al.

(10) Patent No.: US 6,221,986 B1
(45) Date of Patent: Apr. 24, 2001

(54) PROCESS FOR CONVERTING ETHYLENE TO LIGHT ALPHA OLEFINS

(75) Inventors: Dominique Commereuc, Meudon; Serge Boivineau, Oullins; François Hugues, Vernaison; Lucien Saussine, Croissy sur Seine, all of (FR)

(73) Assignee: Institut Francais du Petrole, Rueil-Malmaison Cedex (FR)

( * ) Notice: Subject to any disclaimer, the term of this patent is extended or adjusted under 35 U.S.C. 154(b) by 0 days.

(21) Appl. No.: 09/604,238

(22) Filed: Jun. 27, 2000

Related U.S. Application Data

(62) Division of application No. 09/030,161, filed on Feb. 25, 1998, now Pat. No. 6,103,654.

(30) Foreign Application Priority Data

Feb. 25, 1997 (FR) .................................. 97 02.328

(51) Int. Cl.[7] .............................. B01J 31/14; B01J 31/38; C08F 4/60
(52) U.S. Cl. .................... 526/160; 526/142; 526/153; 526/161; 526/90; 502/110; 502/117; 502/126; 502/132
(58) Field of Search .................... 502/110, 117, 502/126, 132; 526/142, 153, 160, 161, 90

(56) References Cited

U.S. PATENT DOCUMENTS

| | | | |
|---|---|---|---|
| 3,846,388 | 11/1974 | Ohashi et al. | 260/82.1 |
| 3,919,180 | 11/1975 | Furukawa et al. | 260/80.7 |
| 4,477,586 | 10/1984 | McDaniel | 502/104 |
| 4,533,705 | 8/1985 | Sato et al. | 526/114 |
| 5,292,979 | 3/1994 | Chauvin et al. | 585/523 |
| 5,345,023 | 9/1994 | Chauvin et al. | 585/527 |
| 5,496,783 | 3/1996 | Chauvin et al. | 502/125 |
| 5,629,398 | 5/1997 | Okamoto et al. | 526/281 |
| 5,817,905 | 10/1998 | Commereuc et al. | 585/527 |
| 6,103,654 | 8/2000 | Commereuc et al. | 502/110 |

FOREIGN PATENT DOCUMENTS

| | | |
|---|---|---|
| 43 38 414 | 3/1995 | (DE) . |
| 0 295 960 | 12/1988 | (EP) . |
| 0 320 571 | 6/1989 | (EP) . |
| 444505 A2 * | 9/1991 | (EP) . |
| 0 444 505 | 9/1991 | (EP) . |
| 95/19332 | 7/1995 | (WO) . |

* cited by examiner

Primary Examiner—Mark Kopec
Assistant Examiner—Brian P. Mruk
(74) Attorney, Agent, or Firm—Millen, White, Zelano & Branigan

(57) ABSTRACT

A process for producing light alpha olefins by ethylene oligomerisation in contact with a catalyst produced by mixing a zirconium compound with an organic compound selected from the group formed by acetals and ketals, with an aluminum hydrocarbyl compound selected from the group formed by chlorine-containing or bromine-containing aluminum hydrocarbyl compounds and with an aluminum hydrocarbyl compound selected from tris-(hydrocarbyl)-aluminum compounds.

17 Claims, No Drawings

PROCESS FOR CONVERTING ETHYLENE TO LIGHT ALPHA OLEFINS

This is a divisional of application Ser. No. 09/030,161 filed Feb. 25, 1998. Now U.S. Pat No. 6,103,654

The present invention relates to a process for producing light alpha olefins by oligomerisation of ethylene in contact with a Ziegler-type catalyst produced by mixing a zirconium compound with an organic compound selected from the group formed by acetals and ketals, with an aluminium hydrocarbyl compound selected from the group formed by chlorine-containing or bromine-containing aluminium hydrocarbyl compounds and with an aluminium hydrocarbyl compound selected from tris-(hydrocarbyl)-aluminium compounds.

A number of zirconium compounds have been used to oligomerise ethylene to alpha olefins, generally associated with various other ligands.

Examples are the use of zirconium halides associated with esters, ketones, ethers, amines, nitrites, anhydrides, acid chlorides, amides or aldehydes, described in U.S. Pat. No. 4,855,525 and International patent application WO 91 02707, or the use of the same zirconium halides associated with ligands selected from the group formed by sulphur-containing, phosphorous-containing or nitrogen-containing compounds, described in European patents EP-A-0 241 596 and EP-A-0 328 728.

The products obtained with the catalytic formulae given above are principally constituted by alpha olefins with a chain length of between $C_{10}$ and $C_{18}$.

U.S. Pat. No. 5,345,023 describes a process for producing light alpha olefins, principally 1-butene, 1-hexene, 1-octene and 1-decene, by oligomerising ethylene, using a catalytic composition obtained by mixing a zirconium compound with an organic compound selected from the group formed by acetals and ketals and with a chlorine-containing or bromine-containing aluminium hydrocarbyl compound. The teaching of this patent is included in the present application.

We have now discovered that the addition of a tris-(hydrocarbyl)-aluminium to the above catalytic composition can greatly increase the activity.

More precisely, the improved catalytic composition is obtained by mixing:

at least one zirconium compound with formula $ZrX_xY_yO_z$, where X is a chlorine or bromine atom, Y is a radical selected from the group formed by alkoxy $RO^-$, amido $R_2N^-$, or carboxylate $RCOO^-$ groups, where R is a hydrocarbyl radical containing 1 to 30 carbon atoms, x and y have whole number values of 0 to 4 and z is equal to 0 or 0.5, the sum x+y+2z being equal to 4;

with at least one organic compound with formula $(R_1')(R_2')C(OR_1)(OR_2)$ where $R_1'$ and $R_2'$ are constituted by a hydrogen atom or a hydrocarbyl radical containing 1 to 30 carbon atoms, $R_1$ and $R_2$ being hydrocarbyl radicals containing 1 to 30 carbon atoms;

with at least one aluminium compound with formula $AlR''_nX_{3-n}$ where R" is a hydrocarbyl radical containing 1 to 6 carbon atoms, X is a chlorine or bromine atom, and n is a number in the range 1 to 2;

and with at least one aluminium compound with formula $AlR'''_3$ where R''' is a hydrocarbyl radical containing 1 to 6 carbon atoms.

Preferably, the composition also comprises at least one solvent, advantageously selected from the group formed by aliphatic, cycloaliphatic and aromatic hydrocarbons, and compounds corresponding to by-products of oligomerisation such as high oligomers. The solvent is preferably selected from aromatic hydrocarbons; ortho-xylene is particularly suitable.

Reference should be made to U.S. Pat. No. 5,345,023 for the preparation of the catalytic composition.

Examples of zirconium compounds are zirconium halides such as zirconium tetrachloride $ZrCl_4$, zirconium tetrabromide $ZrBr_4$, alcoholates such as zirconium tetrapropylate $Zr(OC_3H_7)_4$, zirconium tetrabutylate $Zr(OC_4H_9)_4$, carboxylates such as zirconium 2-tetraethyl hexanoate $Zr(OCOC_7H_{15})_4$ or oxocarboxylates such as dizirconium 2-oxohexaethyl hexanoate $[Zr(OCOC_7H_{15})_3]_2O$.

The organic compounds selected from the group formed by acetals and ketals used in the invention result from condensing an aldehyde or ketone with a mono-alcohol or a poly-alcohol, for example a glycol. They have the following general formula:

$$(R_1')(R_2')C(OR_1)(OR_2)$$

where $R_1'$ and $R_2'$ are constituted by a hydrogen atom or a hydrocarbyl radical containing 1 to 30 carbon atoms and $R_1$ and $R_2$ are hydrocarbyl groups containing 1 to 30 carbon atoms. The two radicals $R_1'$ and $R_2'$ and the two radicals $R_1$ and $R_2$ may be identical or different. They can also form a ring. Examples are diethoxymethane, diisopropoxymethane, 1,1-diethoxyethane, 1,1-diisobutoxyethane, 1,1-dimethoxydecane, 2-nonyl- 1,3-dioxolane, 2,2-dimethoxyoctane, 1,1-dimethoxycyclohexane, and preferably 2,2-dimethoxypropane, 2,2-dibutoxypropane, 2,2-dihexyloxypropane, 2,2-dioctoxypropane, and 2,2-di-(2-ethylhexyloxy)-propane.

Examples of the aluminium compounds used in the invention represented by general formula $AlR''_nX_{-n}$ are chlorodiethylaluminium, dichloroethylaluminium, and preferably ethylaluminium sesquichloride, or mixtures thereof.

Examples of the aluminium compounds used in the invention represented by general formula $AlR'''_3$ are trimethylaluminium, tributylaluminium, trihexylaluminium, and preferably triethylaluminium.

Particularly advantageously, the catalyst so resulting from the interaction of a mixture of at least one zirconium compound, such as zirconium tetrachloride, and at least one organic compound selected from the group formed by acetals and ketals, resulting from condensing an aldehyde or a ketone with a mono-alcohol or a poly-alcohol, such as 2,2-di-(2-ethylhexyloxy)-propane, with at least one chlorine-containing or bromine-containing aluminium hydrocarbyl compound, such as ethylaluminium sesquichloride, and with at least one tris-(hydrocarbyl)-aluminium, such as triethylaluminium.

The catalyst components can be brought into contact in any order in a solvent selected from the group formed by aliphatic hydrocarbons and cycloaliphatic hydrocarbons such as hexane, cyclohexane or heptane, aromatic hydrocarbons such as toluene or xylenes, and by-products of oligomerisation such as high oligomers. Advantageously, aromatic hydrocarbons are used, preferably ortho-xylene. The zirconium compound is preferably first mixed with the acetal or ketal then the aluminium compounds are added to the mixture, in any order or themselves as a mixture.

The molar ratio between the acetal or ketal and the zirconium compound is 0.1:1 to 5:1, preferably 0.5:1 to 2:1. The molar ratio between the chlorine-containing or bromine-containing aluminium hydrocarbyl and the zirconium compound is 1:1 to 100:1, preferably 5:1 to 50:1. The molar ratio between the tris-(hydrocarbyl)-aluminium and the zirconium compound is 0.01:1 to 10:1, preferably 0.1:1 to 2:1. The concentration of zirconium in the catalytic solution so prepared is advantageously in the range $10^{-4}$ to 1 mole per liter, preferably $10^{-3}$ to 0.5 moles per liter. The temperature at which the four components are mixed is normally in the range $-10°$ C. to $180°$ C., preferably in the range $0°$ C. to +150° C., for example a temperature close to ambient temperature (15° C. to 30° C.). The mixture can be formed in an atmosphere of ethylene or an inert gas.

The solution or catalytic composition produced as above can be used as it is to carry out the oligomerisation reaction, or it can be diluted by adding a solvent selected from the group formed by aliphatic, cycloaliphatic and aromatic hydrocarbons, and by-products of oligomerisation such as high oligomers. Aromatic hydrocarbons are preferably used, preferably ortho-xylene.

The process is carried out under oligomerisation conditions, at pressures of 0,5 to 15 MPa, and at temperatures of 20–180°0 C.

In a process for carrying out batchwise catalytic oligomerisation, the required volume of the catalytic solution prepared as described above is introduced into a reactor provided with the usual stirring and cooling systems, then pressurised with ethylene to a pressure which is generally in the range 0.5 to 15 MPa, preferably in the range 1 to 10 MPa, and the temperature is generally maintained between 20° C. and 180° C., preferably between 40° C. and 150° C. The oligomerisation reactor is supplied with ethylene at a constant pressure until the total volume of liquid produced represents between 2 and 50 times the volume of the catalytic solution originally introduced. The catalyst is then destroyed, for example by injecting an amine into the reactor, then the reaction products and any solvent are extracted and separated from any solvent.

The operation of a continuous process is preferably as follows: the catalytic solution is injected into the reactor at the same time as the ethylene, the reactor being stirred by conventional mechanical means or by external re-circulation. The catalyst components can also be injected separately into the reaction medium, for example the product of the interaction of the zirconium compound with the acetal or ketal, and the mixture of the two aluminium compounds. The temperature is kept between 20° C. and 180° C., preferably between 40° C. and 150° C., and the pressure is generally adjusted to between 0.5 and 15 MPa, preferably between 1 and 10 MPa. The liquid level in the reactor is kept constant. Ethylene is introduced via an inlet valve, which is pressure controlled, which keeps it constant. The reaction mixture is extracted from the reaction zone using a valve controlled by the liquid level. This mixture is sent to a catalyst destruction zone which comprises injection of an amine, for example, then vaporisation of the effluent treated with the amine, either by raising the temperature, or by reducing the pressure, or by simultaneous action on the temperature and the pressure, to recover the products in the vaporised fraction. The products and any solvent are then separated in a system of distillation columns. The unreacted ethylene can be returned to the reactor. The catalyst residues included in a heavy fraction can be incinerated.

The following examples illustrate the invention without limiting its scope.

EXAMPLE 1

$2 \times 10^{-3}$ moles of sublimed zirconium tetrachloride was transferred into a 100 ml glass flask in an inert atmosphere in the absence of moisture, then 45 ml of dry, de-aerated ortho-xylene was injected using a hypodermic syringe. $2 \times 10^{-3}$ moles of 2,2-di-(2-ethylhexyloxy)-propane in solution in 5 ml of ortho-xylene was added to the white suspension, which was stirred at ambient temperature using a magnetic stirrer. Over a period of several minutes, the zirconium chloride dissolved and a homogeneous yellow solution formed.

5 ml of the solution of the zirconium complex formed above, i.e., $0.2 \times 10^{-3}$ moles of zirconium, 50 ml of ortho-xylene, then a mixture of $0.2 \times 10^{-3}$ moles of triethylaluminium and $1.2 \times 10^{-3}$ moles of ethylaluminium sesquichloride $Al_2Et_3Cl3$ in solution in 10 ml of ortho-xylene were introduced in that order into a stainless steel autoclave with a working volume of 250 ml provided with a double envelope to regulate the temperature by circulating oil or water, in an argon atmosphere at ambient temperature. The temperature was then raised to 90° C. while introducing ethylene into the autoclave so as to keep the pressure at a constant 6 MPa.

After 2 hours of reaction, ethylene introduction was stopped. $5 \times 10^{-3}$ moles of 2-ethylhexylamine in solution in 3 ml of ortho-xylene was then injected into the autoclave under pressure using a trap which could be pressurised to a pressure above that of the autoclave. The autoclave was then depressurised and a gaseous fraction and liquid fraction were recovered which were analysed by chromatography.

The material balance of the reaction showed it to be formed of 92.3 g of oligomers, corresponding to a specific activity of 10140 g of oligomers/g of zirconium/hour. The oligomer composition was as follows:

| butenes | 25.2% by weight | 1-butene | 98.8% |
|---|---|---|---|
| hexenes | 22.6 | 1-hexene | 96.5 |
| octenes | 16.9 | 1-octene | 94.0 |
| decenes | 12.9 | 1-decene | 86.6 |
| heavy compounds | 22.4 | | |

EXAMPLE 2

Comparative

This example used the same procedure as that described for Example 1 to prepare the zirconium complex solution. The catalyst was used in the same autoclave, but the triethylaluminium was omitted and the only aluminium compound used was thus ethylaluminium sesquichloride in the same quantity and at the same concentration as that of Example 1.

The ethylene oligomerisation reaction was carried out under the same conditions as in Example 1 and over the same reaction period. At the end of the reaction, 2-ethylhexylamine was injected into the autoclave in the same quantities and using the same technique as described for Example 1.

The material balance of the reaction showed it to be formed of 59 g of oligomers, corresponding to a specific activity of 6486 g of oligomers/g of zirconium/hour. The oligomer composition was as follows:

| butenes | 25.5% by weight | 1-butene | 96.2 |
|---|---|---|---|
| hexenes | 24.1 | 1-hexene | 95.8 |
| octenes | 17.7 | 1-octene | 93.9 |
| decenes | 13 | 1-decene | 85.6 |
| heavy compounds | 19.7 | | |

Comparison of this example of the prior art with Example 1, which was in accordance with the invention, shows the clear superiority of the invention.

EXAMPLE 3

The reaction was carried out in a pilot unit operating in continuous mode. It comprised a perfectly stirred reactor with a total volume of 3 liters, operating with a liquid level control of 2 liters. In this reactor, where the temperature was regulated to 135° C. by oil circulation and the pressure was maintained at 8.5 MPa using a valve located on the ethylene inlet line, 17.2 g/h of a solution of 1 kg of ortho-xylene containing 0.37 g of sublimed zirconium chloride and 0.45 g of 2,2-di-(2-ethylhexyloxy)-propane, and 17.2 g/h of a solution of 1 kg of ortho-xylene containing 5.9 g of aluminium sesquichloride and 0.19 g of triethylaluminium, also 493 g/h of ortho-xylene, were continuously injected.

Under these conditions, the ethylene flow rate at the reactor inlet, which was pressure controlled, settled at 259 g/h. The oligomer production was 136 g/h, corresponding to a productivity of 54.5 kg/g Zr. The oligomer composition was as follows:

| butenes | 28.6 % by weight | 1-butene | 99.7% |
|---|---|---|---|
| hexenes | 25.0 | 1-hexene | 98.1 |
| octenes | 18.3 | 1-octene | 96.4 |
| decenes | 12.2 | 1-decene | 93.0 |
| heavy compounds | 15.9 | | |

EXAMPLE 4

Comparative

The reaction was carried out in the same apparatus using the same procedure as described in the previous example. In this reactor, where the temperature was regulated to 135° C. by oil circulation and the pressure was maintained at 8.5 MPa using a valve located on the ethylene inlet line, 26 g/h of a solution of 1 kg of ortho-xylene containing 0.38 g of sublimed zirconium chloride and 0.46 g of 2,2-di-(2-ethylhexyloxy)-propane, and 26 g/h of a solution of 1 kg of ortho-xylene containing 5.9 g of aluminium sesquichloride, also 508 g/h of ortho-xylene, were continuously injected.

Under these conditions, the ethylene flow rate at the reactor inlet, which was pressure controlled, settled at 273 g/h. The oligomer production was 130 g/h, corresponding to a productivity of 34.1 kg/g Zr. The oligomer composition was as follows:

| butenes | 28.8 % by weight | 1-butene | 99.5 |
|---|---|---|---|
| hexenes | 26.4 | 1-hexene | 97.7 |
| octenes | 18.6 | 1-octene | 95.8 |
| decenes | 11.6 | 1-decene | 90.6 |
| heavy compounds | 14.6 | | |

Comparison of this example with Example 3 clearly demonstrates the advantage of the catalyst of the invention.

What is claimed is:

1. A process for converting ethylene to light alpha olefins comprising oligomerizing ethylene under oligomerization conditions in contact with a catalytic composition obtained by mixing:

at least one zirconium compound with formula $ZrX_xY_yO_z$, where X is a chlorine or bromine atom, Y is a radical selected from the group consisting of alkoxy RO, amido $R_2N$, and carboxylate RCOO groups, where R is a hydrocarbyl radical containing 1 to 30 carbon atoms, x and y have whole number values of 0 to 4 and z is equal to 0 or 0.5, the sum x+y+2z being equal to 4;

with at least one organic compound with formula $(R_1')(R_2')C(OR_1)(OR_2)$ where $R_1'$ and $R_2'$ being a hydrogen atom or hydrocarbyl radicals containing 1 to 30 carbon atoms, and $R_1$ and $R_2$ being hydrocarbyl radicals containing 1 to 30 carbon atoms;

with at least one aluminum compound with formula $AlR''_nX_{3-n}$ where R" is a hydrocarbyl radical containing 1 to 6 carbon atoms, X is a chlorine or bromine atom, and n is a number in the range 1 to 2;

and with at least one, tris-(hydrocarbyl) aluminum compound with formula $AlR'''_3$ where R'" is a hydrocarbyl radical containing 1 to 6 carbon atoms.

2. A process according to claim 1, characterized in that the catalytic composition also contains at least one solvent selected from the group consisting of aliphatic, cycloaliphatic and aromatic hydrocarbons, and high oligomer by products of oligomerisation.

3. A process according to claim 2, characterized in that the solvent is an aromatic hydrocarbon.

4. A process according to claim 3, characterized in that the solvent is ortho-xylene.

5. A process according to claim 1, characterized in that the zirconium compound and the organic compound are mixed, the product obtained then being mixed with the aluminium compounds.

6. A process according to of claim 1, characterized in that the organic compound is diethoxymethane, diisopropoxymethane, 1,1-diethoxyethane, 1,1-diisobutoxyethane, 1,1-dimethoxydecane, 2-nonyl-1,3-dioxolane, 2,2-dimethoxyoctane, 1,1-dimethoxycyclohexane, 2,2-dimethoxypropane, 2,2-dibutoxypropane, 2,2-dihexyloxypropane, 2,2-dioctoxypropane, or 2,2-di-(2-ethylhexyloxy)-propane.

7. A process according to claim 1, characterized in that the zirconium compound is zirconium tetrachloride.

8. A process according to claim 1 characterized in that the two aluminium compounds are ethylaluminium sesquichloride and triethylaluminium.

9. A process according to claim 1, characterized in that the molar ratio between the organic compound and the zirconium compound is in the range 0.1:1 to 5:1.

10. A processed according to claim 1, characterized in that the molar ratio between the chlorine-containing or bromine-containing aluminium hydrocarbyl and the zirconium compound is in the range 1:1 to 100:1.

11. A process according to claim 1, characterized in that the molar ratio between the tris-(hydrocarbyl)-aluminium compound and the zirconium compound is in the range 0.01:1 to 10:1.

12. A process according to claim 1, characterized in that the catalyst components are mixed at a temperature which is in the range −10° C. to 180° C.

13. A process according to claim 2, characterized in that the solvent is used during mixing of the compounds.

14. A process according to claim 7, characterized in that the two aluminum compounds are ethylaluminum sesquichloride and triethylaluminum.

15. A process according to claim 14, characterized in that the molar ratio between the chlorine-containing or bromine-containing aluminum hydrocarbyl and the zirconium compound is in the range 1:1 to 100:1.

16. A process according to claim 15, characterized in that the molar ratio between the tris-(hydrocarbyl)-aluminum compound and the zirconium compound is in the range 0.01:1 to 10:1.

17. A process according to claim 16, characterized in that the molar ratio between the organic compound and the zirconium compound is in the range 0.1:1 to 5:1.

* * * * *

UNITED STATES PATENT AND TRADEMARK OFFICE
CERTIFICATE OF CORRECTION

| | |
|---|---|
| PATENT NO. | : 6,221,986 B1 |
| APPLICATION NO. | : 09/604238 |
| DATED | : April 24, 2001 |
| INVENTOR(S) | : Dominique Commereuc et al. |

It is certified that error appears in the above-identified patent and that said Letters Patent is hereby corrected as shown below:

Column 6, line 3, reads "oligonerizing" should read -- oligomerizing --
Column 6, line 14, reads "$R_{1' \text{ and } R2}$'" should read -- $R_1$' and $R_2$' --

Signed and Sealed this

Twenty-seventh Day of February, 2007

JON W. DUDAS
*Director of the United States Patent and Trademark Office*